(12) United States Patent
Pearl, Jr. et al.

(10) Patent No.: US 10,344,197 B2
(45) Date of Patent: Jul. 9, 2019

(54) SYSTEMS AND METHODS FOR ANALYZING THE CHARACTERISTICS AND COMPOSITIONS OF CEMENT ADDITIVES

(71) Applicant: Halliburton Energy Services, Inc., Houston, TX (US)

(72) Inventors: William C. Pearl, Jr., Houston, TX (US); Megan Renee Pearl, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 284 days.

(21) Appl. No.: 15/313,283

(22) PCT Filed: Aug. 26, 2014

(86) PCT No.: PCT/US2014/052640
§ 371 (c)(1),
(2) Date: Nov. 22, 2016

(87) PCT Pub. No.: WO2016/032438
PCT Pub. Date: Mar. 3, 2016

(65) Prior Publication Data
US 2017/0190946 A1    Jul. 6, 2017

(51) Int. Cl.
*E21B 33/13*    (2006.01)
*C09K 8/42*    (2006.01)
(Continued)

(52) U.S. Cl.
CPC .............. *C09K 8/42* (2013.01); *C04B 28/02* (2013.01); *C04B 40/0096* (2013.01);
(Continued)

(58) Field of Classification Search
CPC .... E21B 47/0005; E21B 47/102; E21B 33/13; C09K 8/42; C09K 8/467; G01J 3/36;
(Continued)

(56) References Cited

U.S. PATENT DOCUMENTS 4,618,939 A   10/1986 Davis
5,027,267 A    6/1991 Pitts et al.
(Continued)

FOREIGN PATENT DOCUMENTS

WO    2014052182 A1    4/2014
WO    2016032438 A1    3/2016

OTHER PUBLICATIONS

Brost et al., "Optical Methods for Monitoring Treating Chemicals in Oilfield Water Systems," SPE 22781, 217-232, 1991.
(Continued)

*Primary Examiner* — Brad Harcourt
(74) *Attorney, Agent, or Firm* — Gilliam IP PLLC

(57) ABSTRACT

Optical analysis systems and methods may be used for analyzing the characteristics, including compositions, of cement additives, which may be used in formulating a cement slurry. For example, a cement additive may be optically interacting with an integrated computational element ("ICE") configured to detect a characteristic of the cement additive. An output signal may then be generated corresponding to the characteristic of the cement additive detected by the ICE, which may be received and processed with a signal processor to yield a value for the characteristic of the cement additive. The value of the characteristic of the cement additive may then be used to determine an amount of the cement additive for use in producing a cement slurry.

19 Claims, 2 Drawing Sheets

(51) Int. Cl.
| | |
|---|---|
| *E21B 47/00* | (2012.01) |
| *E21B 47/10* | (2012.01) |
| *G01J 3/00* | (2006.01) |
| *G01N 21/31* | (2006.01) |
| *G01N 33/38* | (2006.01) |
| *G01N 21/85* | (2006.01) |
| *C04B 28/02* | (2006.01) |
| *C04B 40/00* | (2006.01) |
| *C09K 8/467* | (2006.01) |
| *G01J 3/12* | (2006.01) |
| *G01J 3/36* | (2006.01) |
| *G01J 3/457* | (2006.01) |
| *G01N 21/76* | (2006.01) |

(52) U.S. Cl.
CPC .............. *C09K 8/467* (2013.01); *E21B 33/13* (2013.01); *E21B 47/0005* (2013.01); *E21B 47/102* (2013.01); *G01J 3/00* (2013.01); *G01J 3/12* (2013.01); *G01J 3/36* (2013.01); *G01J 3/457* (2013.01); *G01N 21/31* (2013.01); *G01N 21/85* (2013.01); *G01N 33/383* (2013.01); *G01J 2003/1226* (2013.01); *G01J 2003/1282* (2013.01); *G01N 21/76* (2013.01)

(58) Field of Classification Search
CPC ...... G01J 3/12; G01J 3/457; G01J 3/00; G01J 2003/1226; G01J 2003/1282; G01N 21/85; G01N 21/31; G01N 33/383; G01N 21/76
See application file for complete search history.

(56) References Cited

U.S. PATENT DOCUMENTS

| | | | |
|---|---|---|---|
| 5,400,137 | A | 3/1995 | Winslow et al. |
| 5,418,614 | A | 5/1995 | Brost et al. |
| 5,489,977 | A | 2/1996 | Winslow et al. |
| 6,198,531 | B1 | 3/2001 | Myrick et al. |
| 6,529,276 | B1 | 3/2003 | Myrick |
| 7,123,844 | B2 | 10/2006 | Myrick |
| 7,138,156 | B1 | 11/2006 | Myrick et al. |
| 7,472,748 | B2 | 1/2009 | Gdanski et al. |
| 7,623,233 | B2 | 11/2009 | Freese et al. |
| 7,697,141 | B2 | 4/2010 | Jones et al. |
| 7,712,527 | B2 | 5/2010 | Roddy |
| 7,834,999 | B2 | 11/2010 | Myrick et al. |
| 7,911,605 | B2 | 3/2011 | Myrick et al. |
| 7,920,258 | B2 | 4/2011 | Myrick et al. |
| 7,938,175 | B2 | 5/2011 | Skinner et al. |
| 8,049,881 | B2 | 11/2011 | Myrick et al. |
| 8,141,633 | B2 | 3/2012 | Hampton et al. |
| 2006/0027144 | A1 | 2/2006 | Chatterji et al. |
| 2007/0282647 | A1 | 12/2007 | Freese et al. |
| 2008/0231849 | A1 | 9/2008 | Myrick et al. |
| 2008/0276687 | A1 | 11/2008 | Myrick et al. |
| 2009/0073433 | A1 | 3/2009 | Myrick et al. |
| 2009/0097024 | A1 | 4/2009 | Blackburn et al. |
| 2009/0140144 | A1 | 6/2009 | Myrick et al. |
| 2009/0182693 | A1 | 7/2009 | Fulton et al. |
| 2009/0216504 | A1 | 8/2009 | Priore et al. |
| 2009/0219512 | A1 | 9/2009 | Myrick et al. |
| 2009/0219538 | A1 | 9/2009 | Myrick et al. |
| 2009/0219539 | A1 | 9/2009 | Myrick et al. |
| 2009/0250613 | A1 | 10/2009 | Myrick et al. |
| 2009/0299946 | A1 | 12/2009 | Myrick et al. |
| 2009/0316150 | A1 | 12/2009 | Myrick et al. |
| 2010/0050905 | A1 | 3/2010 | Lewis et al. |
| 2010/0051266 | A1 | 3/2010 | Roddy et al. |
| 2010/0051275 | A1 | 3/2010 | Lewis et al. |
| 2010/0073666 | A1 | 3/2010 | Perkins et al. |
| 2010/0141952 | A1 | 6/2010 | Myrick et al. |
| 2010/0149537 | A1 | 6/2010 | Myrick et al. |
| 2010/0153048 | A1 | 6/2010 | Myrick et al. |
| 2010/0182600 | A1 | 7/2010 | Freese et al. |
| 2010/0195105 | A1 | 8/2010 | Myrick et al. |
| 2010/0245096 | A1 | 9/2010 | Jones et al. |
| 2010/0265509 | A1 | 10/2010 | Jones et al. |
| 2010/0302539 | A1 | 12/2010 | Myrick et al. |
| 2010/0305741 | A1 | 12/2010 | Myrick |
| 2010/0328669 | A1 | 12/2010 | Myrick et al. |
| 2011/0132606 | A1 | 6/2011 | Demong et al. |
| 2011/0199610 | A1 | 8/2011 | Myrick et al. |
| 2011/0308788 | A1 | 12/2011 | Ravi et al. |
| 2012/0205103 | A1 | 8/2012 | Ravi et al. |
| 2014/0076549 | A1 | 3/2014 | Pelletier et al. |

OTHER PUBLICATIONS

Myrick, et al. "Spectral Tolerance Determination for Multivariate Optical Element Design," Fresenuis' Journal of Analytical Chemistry, 369:2001; pp. 351-355.

Ramachandran, et al., "Chemical Kinetics in Real Time: Using the Differential Rate Law and Discovering the Reaction Orders," A Physical Chemistry Laboratory Experiment, Journal of Chemical Education; 1996, pp. 686-689.

International Search Report and Written Opinion for PCT/US2014/052640, dated May 27, 2015.

SYSTEMS AND METHODS FOR ANALYZING THE CHARACTERISTICS AND COMPOSITIONS OF CEMENT ADDITIVES

BACKGROUND

The exemplary embodiments described herein relate to systems and methods for analyzing cement additives.

Set cement compositions are used in the oil and gas sector for many purposes including stabilizing wellbores and plugging wellbores. Set cements are produced from cement slurries that include hydraulic cements in water with other cement additives. The operational parameters relating to the cement slurry and the properties of the resultant set cement are derived, at least in part, from the composition and concentration of the cement additives. For example, set retarders and set accelerators are used to establish a set time for the cement slurry that provides sufficient time to place the cement slurry in a predetermined location without having to wait too long for the cement to set once placed. In other examples, fillers may be used to achieve desired mechanical properties in the set cement (e.g., ground marble to increase the compressive strength and rubber to increase yield strength). Additionally, fillers like gas may be used to increase the permeability of the set cement.

Cement slurry formulations are developed to take into account the effects of each of the cement additives to yield the desired cement slurry operational parameters and set cement properties. Variations in the quality or quantity of any of the cement additives may affect the cement slurry operational parameters and set cement properties. For example, increased salt concentration from the water supply or another cement additive may accelerate or retard the set time of the cement slurry depending on concentration. Increasing the set time increases the cost of the cementing operation because of the nonproductive time associated with waiting for the cement slurry to set. In another example, magnesium salts like magnesium chloride, which can be a contaminant in silica fillers and some water supplies, expand after the cement slurry has set causing cracks and leaks in the set cement. Costly remedial operations may then need to be performed to plug the cracks.

Generally, the composition of cement additives is analyzed after production. However, the composition of the cement additives may change over time, for example, due to storage time, shipping conditions, storage conditions at the manufacture or at the well site, and the like. Compositional changes that may arise then allow for producing cement slurries that are not in spec with the developed cement slurry formulation, which as described above may have costly and time consuming results.

BRIEF DESCRIPTION OF THE DRAWINGS

The following figures are included to illustrate certain aspects of the exemplary embodiments described herein, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
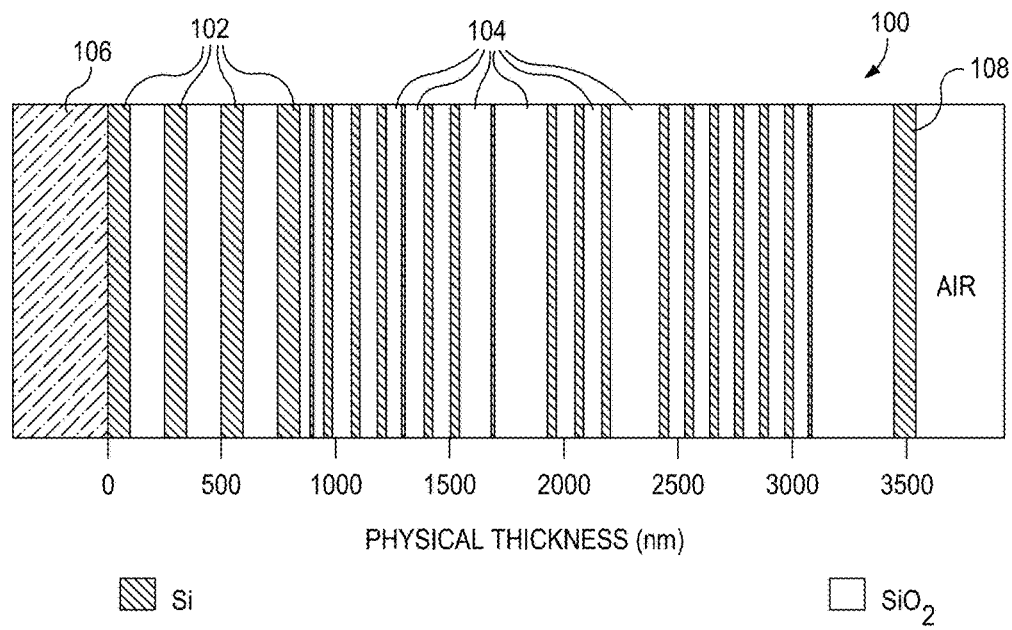
FIG. 1 illustrates an exemplary integrated computation element, according to one or more embodiments.

The exemplary embodiments described herein relate to optical analysis systems and methods for analyzing the characteristics, including compositions, of cement additives.

The exemplary systems and methods described herein employ various configurations of optical computing devices, also commonly referred to as "opticoanalytical devices," for the rapid analysis of cement additives. The disclosed systems and methods may be suitable for use in the oil and gas industry since the described optical computing devices provide a cost-effective, rugged, and accurate means for analyzing the composition of cement additives in order to facilitate the effective production of cement slurries and set cements in oil/gas applications. It will be appreciated, however, that the various disclosed systems and methods are equally applicable to other technology fields including, but not limited to, the food and drug industry, industrial applications, mining industries, or any field where it may be advantageous to determine in real-time or near real-time a characteristic of a dry composition, especially to determine the quality of the dry composition.

The optical computing devices disclosed herein, which are described in more detail below, can advantageously provide rapid analysis of at least one characteristic of a cement additive (e.g., the composition of individual analytes in the cement additive, the presence or absence of contaminants in the cement additive, or the relative concentration of two or more analytes in the cement additive). As described above, such a detailed analysis is generally performed just after production of the cement additive and not again after contamination or degradation may occur. The optical computing devices disclosed herein may provide rapid analysis of cement additives, which can be implemented at various points along the supply and implementation chain for the cement additive, including at the well site where a cement slurry is produced. Additionally, because the analysis is rapid, multiple measurements may be taken to reduce error.

A significant and distinct advantage of the optical computing devices disclosed herein is that they can be configured to specifically detect and/or measure a particular characteristic of interest of a cement additive, thereby allowing for qualitative and/or quantitative analyses of the cement additive. With rapid analysis capabilities on hand, the exemplary systems and methods described herein may be able to determine the composition and/or concentration of the cement additive so that changes to the cement slurry formulation, for example, to counteract a contaminant in the cement additive, may be implemented, thereby increasing the efficacy and efficiency of the cementing operation. Additionally, such analysis may allow for the collection and archival of information relating to the cement additive in conjunction with operational information to optimize subsequent operations.

As used herein, the term "hydraulic cement" refers to inorganic cementitious materials of known type which comprise compounds of calcium, aluminum, silicon, oxygen and/or sulfur which exhibit "hydraulic activity," that is, which set solid and harden in the presence of water. Hydraulic cements may comprise a single cement or comprise a blend of two or more cements. Examples of hydraulic cements may include, but are not limited to, hydraulic cements, Portland cement, gypsum cements, pozzolan cements, calcium phosphate cements, high alumina content cements, silica cements, high alkalinity cements, shale cements, acid/base cements, magnesia cements (e.g., Sorel cements), zeolite cement systems, cement kiln dust cement systems, slag cements, micro-fine cements, bentonites, and the like, any derivative thereof, and any combination thereof. Examples of Portland cements may include, but are not limited to, Portland cements classified as Classes A, C, H, and G according to API and their equivalent, Ordinary Portland cements of Type I, I/II, III, and V according to ASTM, including combinations thereof. Examples of pozzolan cements may include, but are not limited to, fly ash, silica fume, granulated blast furnace slag, calcined shale, opaline shale, pumice, pumicite, diatomaceous earth, volcanic ash, tuft, cement kiln dust, and any combination thereof.

As used herein, the term "cement additive" refers to an additive that can be included in a cement slurry with a dry cement. For the purposes of this disclosure, the water is considered a cement additive. Cement additives may be liquids (e.g., concentrates) or dry additives (e.g., powders). In some instances, the dry cement and at least one dry cement additive may be combined to form a mixture that can be used in preparing a cement slurry. The mixture may be prepared at a storage facility, manufacturing facility, laboratory, distribution center, or well site or in transit between any of these locations.

Examples of cement additives may include, but are not limited to, water, set retarders, set accelerators, fillers, dispersants, gelling agents, fluid-loss controllers and the like, and any combination thereof. Examples of sources for the water may include fresh water, saltwater (e.g., water containing one or more salts dissolved therein), brine (e.g., saturated salt water), seawater, produced water (i.e., water produced from a subterranean formation typically at the well site), and any combination thereof. Examples of set retarders may include ammonium, alkali metals, alkaline earth metals, a phosphonic acid, a phosphonic acid derivative, a lignosulfonate (e.g., sodium lignosulfonate), metal salts of sulfoalkylated lignins, a salt, a borate compound, an organic acid, a hydroxycarboxy acid, a carboxymethylated hydroxyethylated cellulose, a co- or ter-polymer comprising acrylic acid or maleic acid, a synthetic co- or ter-polymer comprising sulfonate groups and carboxylic acid groups, a co- or ter-polymer of acrylic acid and acrylamido-methyl-propane sulfonate polymer, a co- or ter-polymer of maleic anhydride and acrylamido-methyl-propane sulfonate polymer, and any combination thereof. Examples of set accelerators may include calcium chloride, triethanolamine, sodium silicate, zinc formate, calcium formate, calcium acetate, calcium nitrate, sodium hydroxide, sodium sulfate, and any combination thereof. Examples of fillers may include sand, barite, calcium carbonate, ground marble, iron oxide, manganese oxide, glass beads, crushed glass, crushed drill cuttings, ground vehicle tires, crushed rock, ground asphalt, crushed concrete, crushed cement, salt, ilmenite, hematite, elastomers, polymers, nitrogen, air, fibers, any derivative thereof, and combinations thereof. Examples of polymer fillers include, but are not limited to, natural rubber, acrylate butadiene rubber, polyacrylate rubber, isoprene rubber, chloroprene rubber, butyl rubber, brominated butyl rubber, chlorinated butyl rubber, chlorinated polyethylene, neoprene rubber, styrene butadiene copolymer rubber, sulphonated polyethylene, ethylene acrylate rubber, epichlorohydrin ethylene oxide copolymer, ethylene propylene rubber, ethylene propylene diene terpolymer rubber, ethylene vinyl acetate copolymer, fluorosilicone rubbers, silicone rubbers, poly-2,2,1-bicycloheptene (polynorborneane), alkylstyrene, cross-linked substituted vinyl acrylate copolymer, nitrile rubber (butadiene acrylonitrile copolymer), hydrogenated nitrile rubber, fluoro rubbers, perfluoro rubbers, tetrafluoroethylene/propylene, starch polyacrylate acid graft copolymer, polyvinyl alcolcyclic acid anhydride graft copolymer, isobutylene maleic anhydride, acrylic acid type polymer, vinylacetate-acrylate copolymer, polyethylene oxide polymers, carboxymethyl cellulose polymers, starch-polyacrylonitrile graft copolymers, polymethacrylate, polyacrylamide, non-soluble acrylic polymers, any, and any combination thereof. Examples of dispersants may include sodium oleate, sodium dodecylbenzenesulfonate, sodium decanoate, sodium octyl sulfate, sodium caprylate sodium stearate, sodium myristate, sodium laurate, sodium cetyl sulfate, sodium myristyl sulfate, sodium lauryl sulfate, sodium decyl sulfate, stearyltrimethylammonium chloride, cetyltrimethylammonium tosylate, octyltrimethylammonium chloride, erucyl bis-(hydroxyethyl)methylammonium chloride, erucyl trimethylammonium chloride cetyltrimethylammonium chloride, cetyltrimethylammonium bromide, myristyltrimethylammonium chloride, myristyltrimethylammonium bromide, dodecyltrimethylammonium chloride, dodecyltrimethylammonium bromide, decyltrimethylammonium chloride, decyltrimethylammonium bromide, cocobetaine, cocoamidoethyl betaine, cocoamidopropyl betaine, lauryl betaine, lauramidopropyl betaine, palmamidopropyl betaine, stearamidopropyl betaine, stearyl betaine, lauryldimethyl betaine, cetyldimethyl betaine, hydrogenated cocoamidopropyl betaine, stripped coco(methyl ester)amidopropyl betaine, and any combination thereof. Examples of gelling agents may include polysaccharides, biopolymers, 2,2'-azobis(2,4-dimethyl valeronitrile), 2,2'-azobis(2,4-dimethyl-4-methoxy valeronitrile), polymers and copolymers of acrylamide ethyltrimethyl ammonium chloride, acrylamide, acrylamido- and methacrylamido-alkyl trialkyl ammonium salts, acrylamidomethylpropane sulfonic acid, acrylamidopropyl trimethyl ammonium chloride, acrylic acid, dimethylaminoethyl methacrylamide, dimethylaminoethyl methacrylate, dimethylaminopropyl methacrylamide, dimethylaminopropylmethacrylamide, dimethyldiallylammonium chloride, dimethylethyl acrylate, fumaramide, methacrylamide, methacrylamidopropyl trimethyl ammonium chloride, methacrylamidopropyldimethyl-n-dodecylammonium chloride, methacrylamidopropyldimethyl-n-octylammonium chloride, methacrylamidopropyltrimethylammonium chloride, methacryloylalkyl trialkyl ammonium salts, methacryloylethyl trimethyl ammonium chloride, methacrylylamidopropyldimethylcetylammonium chloride, N-(3-sulfopropyl)-N-methacrylamidopropyl-N,N-dimethyl ammonium betaine, N,N-dimethylacrylamide, N-methylacrylamide, nonylphenoxypoly(ethyleneoxy)ethylmethacrylate, partially hydrolyzed polyacrylamide, poly 2-amino-2-methyl propane sulfonic acid, polyvinyl alcohol, sodium 2-acrylamido-2-methylpropane sulfonate, quaternized dimethylaminoethylacrylate, quaternized dimethylaminoethylmethacrylate, and any combination thereof. Examples of fluid-loss controllers may include polypeptide, ethylene diamine carboxymethylcellulose and other cellulose derivatives, natural and modified polysaccharides, non-ionic synthetic polymers and anionic synthetic polymers.

As used herein, the term "active component" refers to the analyte that performs the function of the material of interest. For example, the active component of a set accelerator is the analyte or analytes that accelerate the setting of the cement. In another example, the active component of a gelling agent is the analyte or analytes that increase the viscosity of the fluid in which the gelling agent is implemented.

As used herein, the term "characteristic" refers to a chemical, mechanical, or physical property (quantitative or qualitative) of a material of interest (e.g., a cement additive or an analyte thereof). As used herein, the term "analyte" refers to a chemical component. The term analyte encompasses chemical components that are at least one of: present in the material of interest (e.g., a contaminant or one component of a two-component additive), may be added to the material of interest, involved in a chemical reaction (e.g., reagents and products) transpiring within the material of interest, and not involved in a chemical reaction transpiring within the material of interest. Illustrative characteristics of a material of interest that can be monitored with the optical computing devices disclosed herein can include, for example, the active component(s) (e.g., identity and concentration in total or of individual analytes that are active components), impurity content (e.g., identity and concentration in total or of individual analytes that are contaminants), a degradation product of the cement additive (e.g., identity and concentration in total or of individual analytes that are degradation products of active components), pH, viscosity, density, ionic strength, total dissolved solids, salt content, porosity, opacity, bacteria content, particle size distribution, color, temperature, hydration level, oxidation state, and the like. Moreover, the phrase "characteristic of interest" may be used herein to refer to a characteristic of a material of interest.

Examples of analytes within a cement additive may include, but are not limited to, the cement additives (e.g., the compound, the polymer, or the mineral that is the cement additive), byproducts of the synthesis of the cement additive (e.g., unreacted reagents like monomers or ungrafted polymer), free lime, inorganic salts (e.g., sodium, potassium, magnesium, and calcium salts of chloride, sulfate, phosphate, and carbonate), metal containing compounds (e.g., bromide, chloride, nitrate, sulfate, and phosphate salts of cadmium, zinc, nickel, copper, lead, and the like, metal oxides of such metals, and the like), hydroxides, clays, (e.g., smectite, bentonite, and attapulgite), organic matter (e.g., humic acid, lignins, hydroxycarboxylic acids, cellulose, saccharides, and carbohydrates such as pentoses, hexoses, and aldonic acids), and any combination thereof.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation from a substance or sample of the substance, and produce an output of electromagnetic radiation from a processing element arranged within the optical computing device. The processing element may be, for example, an integrated computational element (ICE) used in the optical computing device. As discussed in greater detail below, the electromagnetic radiation that optically interacts with the processing element is changed so as to be readable by a detector, such that an output of the detector can be correlated to at least one characteristic of the substance being measured or monitored. The output of electromagnetic radiation from the processing element can be reflected electromagnetic radiation, transmitted electromagnetic radiation, and/or dispersed electromagnetic radiation. Whether reflected or transmitted electromagnetic radiation is analyzed by the detector may be dictated by the structural parameters of the optical computing device as well as other considerations known to those skilled in the art. In addition, emission and/or scattering by the substance, for example via fluorescence, luminescence, Raman scattering, and/or Raleigh scattering, can also be monitored by the optical computing devices.

As used herein, the term "optically interact" or variations thereof refer to the reflection, transmission, scattering, diffraction, or absorption of electromagnetic radiation either on, through, or from one or more processing elements (i.e., integrated computational elements). Accordingly, optically interacted light refers to electromagnetic radiation that has been reflected, transmitted, scattered, diffracted, or absorbed by, emitted, or re-radiated, for example, using the integrated computational elements, but may also apply to interaction with a cement additive.

The exemplary systems and methods described herein will include at least one optical computing device configured to measure at least one characteristic of a cement additive or analyte thereof. In some embodiments, the optical computing devices suitable for use in the exemplary embodiments described herein may be mobile or portable. In some embodiments, the optical computing devices suitable for use in the exemplary embodiments described herein may be a portion of tank, silo, vat, or the like that store, mix, or otherwise contain cement additive (e.g., in a wall).

An optical computing device may include an electromagnetic radiation source, at least one processing element (e.g., an integrated computational element), and at least one detector arranged to receive optically interacted light from the at least one processing element. However, in at least one embodiment, the electromagnetic radiation source may be omitted and instead the electromagnetic radiation may be derived from the material of interest itself. In some embodiments, the exemplary optical computing devices may be specifically configured for detecting, analyzing, and quantitatively measuring a particular characteristic of the material of interest. In other embodiments, the optical computing devices may be general purpose optical devices, with post-acquisition processing (e.g., through computer means) being used to specifically detect the characteristic of interest.

The presently described optical computing devices combine the advantage of the power, precision, and accuracy associated with laboratory spectrometers, while being extremely rugged and suitable for field use. Furthermore, the optical computing devices can perform calculations (analyses) in real-time or near real-time without the need for time-consuming sample processing. In this regard, the optical computing devices can be specifically configured to detect and analyze particular characteristics of interest. As a result, interfering signals are discriminated from those of interest by appropriate configuration of the optical computing devices, such that the optical computing devices provide a rapid response regarding the characteristic of interest as based on the detected output. In some embodiments, the detected output can be converted into a voltage that is distinctive of the magnitude of the characteristic of interest. The foregoing advantages and others make the optical computing devices particularly well suited for field use.

The optical computing devices can be configured to detect not only the composition and concentrations of an analyte in a material of interest, but they can also be configured to determine physical properties and other characteristics of the material of interest as well, based on their analysis of the electromagnetic radiation received from the substance. For example, the optical computing devices can be configured to determine the concentration of an analyte and correlate the determined concentration to a characteristic of the material of interest by using suitable processing means. As will be appreciated, the optical computing devices may be configured to detect as many characteristics as desired for a given material of interest. All that is required to accomplish the monitoring of multiple characteristics of interest is the incorporation of suitable processing and detection means within the optical computing device for each characteristic of interest (e.g., the concentration of an analyte, the particle size distribution, or the temperature). In some embodiments, the properties of the material of interest can be determined using a combination of characteristics of interest (e.g., a linear, non-linear, logarithmic, and/or exponential combination). Accordingly, the more characteristics that are detected and analyzed using the optical computing devices, the more accurately the properties of the material of interest will be determined. For example, properties of a cement additive that may be determined using optical computing devices described herein may include, but are not limited to, the absolute concentration of an analyte, the relative ratios of two or more analytes, the presence or absence of an analyte, and the like, and any combination thereof.

The optical computing devices described herein utilize electromagnetic radiation to perform calculations, as opposed to the hardwired circuits of conventional electronic processors. When electromagnetic radiation interacts with a material of interest, unique physical and chemical information about the material of interest may be encoded in the electromagnetic radiation that is reflected from, transmitted through, or radiated from the material of interest. This information is often referred to as the spectral "fingerprint" of the material of interest. The optical computing devices described herein are capable of extracting the information of the spectral fingerprint of multiple characteristics of a material of interest (e.g., a cement additive or an analyte thereof), and converting that information into a detectable output regarding the overall properties of the monitored material of interest. That is, through suitable configurations of the optical computing devices, electromagnetic radiation associated with characteristics of interest can be separated from electromagnetic radiation associated with all other components of the material of interest in order to estimate the properties (e.g., reactivity) of the monitored substance (e.g., a cement additive or an analyte thereof) in real-time or near real-time.

As indicated above, the processing elements used in the exemplary optical computing devices described herein may be characterized as integrated computational elements (ICE). Each ICE is capable of distinguishing electromagnetic radiation related to the characteristic of interest from electromagnetic radiation related to other components of a cement additive. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and $SiO_2$ (quartz), respectively. In general, these layers 102,104 consist of materials whose index of refraction is high and low, respectively. Other examples might include niobia and niobium, germanium and germania, MgF, $SiO_x$, and other high and low index materials known in the art. The layers 102,104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102,104 and the thickness of each layer 102,104 are determined from the spectral attributes acquired from a spectroscopic analysis of a characteristic of interest using a conventional spectroscopic instrument. The spectrum of interest of a given characteristic of interest typically includes any number of different wavelengths. It should be understood that the exemplary ICE 100 in FIG. 1 does not in fact represent any particular characteristic of interest, but is provided for purposes of illustration only. Consequently, the number of layers 102,104 and their relative thicknesses, as shown in FIG. 1, bear no correlation to any particular characteristic of interest. Nor are the layers 102,104 and their relative thicknesses necessarily drawn to scale, and therefore should not be considered limiting of the present disclosure. Moreover, those skilled in the art will readily recognize that the materials that make up each layer 102,104 (i.e., Si and $SiO_2$) may vary, depending on the application, cost of materials, and/or applicability of the materials to the monitored substance.

In some embodiments, the material of each layer 102,104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), variable optical attenuators, and/or acousto-optic elements, for example, that can create transmission, reflection, and/or absorptive properties of interest.

The multiple layers 102,104 exhibit different refractive indices. By properly selecting the materials of the layers 102,104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102,104 may be determined using a variety of approximation methods from the spectrograph of the characteristic of interest. These methods may include inverse Fourier transform (IFT) of the optical transmission spectrum and structuring the ICE 100 as the physical representation of the IFT. The approximations convert the IFT into a structure based on known materials with constant refractive indices.

The weightings that the layers 102,104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102,104 for each wavelength. As a result, the output light intensity of the ICE 100 is related to the characteristic of interest.

Figure 2:
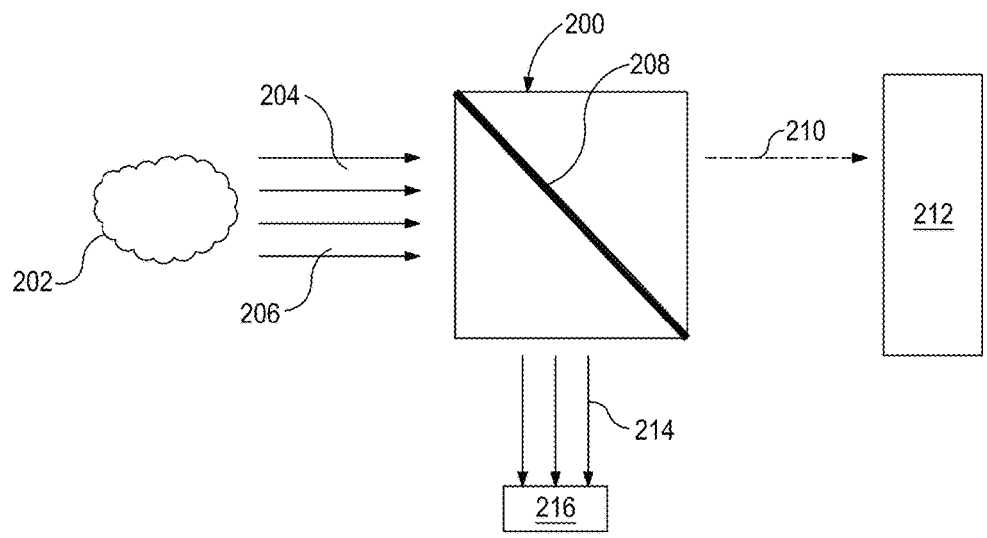
FIG. 2 illustrates a block diagram non-mechanistically illustrating how an optical computing device distinguishes electromagnetic radiation related to a characteristic of interest from other electromagnetic radiation, according to one or more embodiments.

Referring now to FIG. 2, illustrated is a block diagram that non-mechanistically illustrates how an optical computing device 200 is able to distinguish electromagnetic radiation related to a characteristic of interest from other electromagnetic radiation. As shown in FIG. 2, after being illuminated with incident electromagnetic radiation, a cement additive 202 produces an output of electromagnetic radiation (e.g., sample-interacted light), some of which is electromagnetic radiation 204 corresponding to the characteristic of interest and some of which is background electromagnetic radiation 206 corresponding to other characteristics of the cement additive 202. In some embodiments, the cement additive 202 may include one or more characteristics of interest that may correspond to the one or more analytes of the cement additive 202.

Although not specifically shown, one or more processing elements may be employed in the optical computing device 200 in order to restrict the optical wavelengths and/or bandwidths of the system and thereby eliminate unwanted electromagnetic radiation existing in wavelength regions that have no importance. Such processing elements can be located anywhere along the optical train, but are typically employed directly after a light source, which provides the initial electromagnetic radiation.

The beams of electromagnetic radiation 204, 206 impinge upon the optical computing device 200, which contains an exemplary ICE 208 therein. In the illustrated embodiment, the ICE 208 may be configured to produce optically interacted light, for example, transmitted optically interacted light 210 and reflected optically interacted light 214. In operation, the ICE 208 may be configured to distinguish the electromagnetic radiation 204 from the background electromagnetic radiation 206.

The transmitted optically interacted light 210, which may be related to the characteristic of interest of the cement additive 202, may be conveyed to a detector 212 for analysis and quantification. In some embodiments, the detector 212 is configured to produce an output signal in the form of a voltage that corresponds to the particular characteristic of the cement additive 202. In at least one embodiment, the signal produced by the detector 212 and the characteristic of a cement additive 202 (e.g., concentration of an analyte) may be directly proportional. In other embodiments, the relationship may be a polynomial function, an exponential function, and/or a logarithmic function. The reflected optically interacted light 214, which may be related to other characteristics of the cement additive 202, can be directed away from detector 212. In alternative configurations, the ICE 208 may be configured such that the reflected optically interacted light 214 can be related to the characteristic of interest, and the transmitted optically interacted light 210 can be related to other characteristics in the cement additive 202.

In some embodiments, a second detector 216 can be present and arranged to detect the reflected optically interacted light 214. In other embodiments, the second detector 216 may be arranged to detect the electromagnetic radiation 204, 206 derived from the cement additive 202 or electromagnetic radiation directed toward or before the cement additive 202. Without limitation, the second detector 216 may be used to detect radiating deviations stemming from an electromagnetic radiation source (not shown), which provides the electromagnetic radiation (i.e., light) to the device 200. For example, radiating deviations can include such things as, but are not limited to, intensity fluctuations in the electromagnetic radiation, interferent fluctuations (e.g., dust or other interferents passing in front of the electromagnetic radiation source), coatings on windows included with the optical computing device 200, combinations thereof, or the like. In some embodiments, a beam splitter (not shown) can be employed to split the electromagnetic radiation 204, 206, and the transmitted or reflected electromagnetic radiation can then be directed to two or more ICE 208. That is, in such embodiments, the ICE 208 does not function as a type of beam splitter, as depicted in FIG. 2, and the transmitted or reflected electromagnetic radiation simply passes through the ICE 208, being computationally processed therein, before traveling to the detector 212.

The characteristic(s) of interest being analyzed using the optical computing device 200 can be further processed and/or analyzed computationally (e.g., with an algorithm) to provide cement slurry formulation information. For example, contaminants like silica and organic matter in a cement additive 202 may accelerate setting of a cement slurry, and contaminants like organic matter in a cement additive 202 may retard setting of a cement slurry. Additionally, setting of a cement slurry may be accelerated or retarded depending on the salt concentration and pH of a cement additive 202. Accordingly, the amount of set retarder or set accelerator in the cement slurry formulation may be adjusted to counteract the foregoing situations. Additionally, liquid concentrates of cement additives 202 often vary from batch to batch, so knowing the absolute concentration of the cement additives 202 in the liquid concentrates may be advantageous for preparing the cement slurry according to specification. Similarly, some solid cement additives 202 come premixed, and knowing the relative concentrations of two or more analytes in a cement additive 202 may allow for preparing a cement slurry according to specification. In yet another example, some cement additives 202 may degrade over time, and knowing the concentrations of the active analyte in a cement additive 202 may allow for preparing a cement slurry according to specification.

The algorithm can be part of an artificial neural network configured to use the information regarding the cement additive 202 (e.g., as described in the foregoing nonlimiting examples) and predict the composition and/or concentration of the cement additives 202 needed to provide for desired properties in a resultant cement slurry. It is to be recognized that an artificial neural network can be trained using samples of predetermined characteristics of interest, and thereby generating a virtual library. As the virtual library available to the artificial neural network becomes larger, the neural network can become more capable of accurately predicting the characteristic of interest corresponding to a cement additive 202 or analyte thereof. Furthermore, with sufficient training, the artificial neural network can more accurately predict the composition and/or concentration of the cement additive 202, even in the presence of unknown analytes.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a chemical reaction process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site (e.g., via wireless technology).

Figure 3:
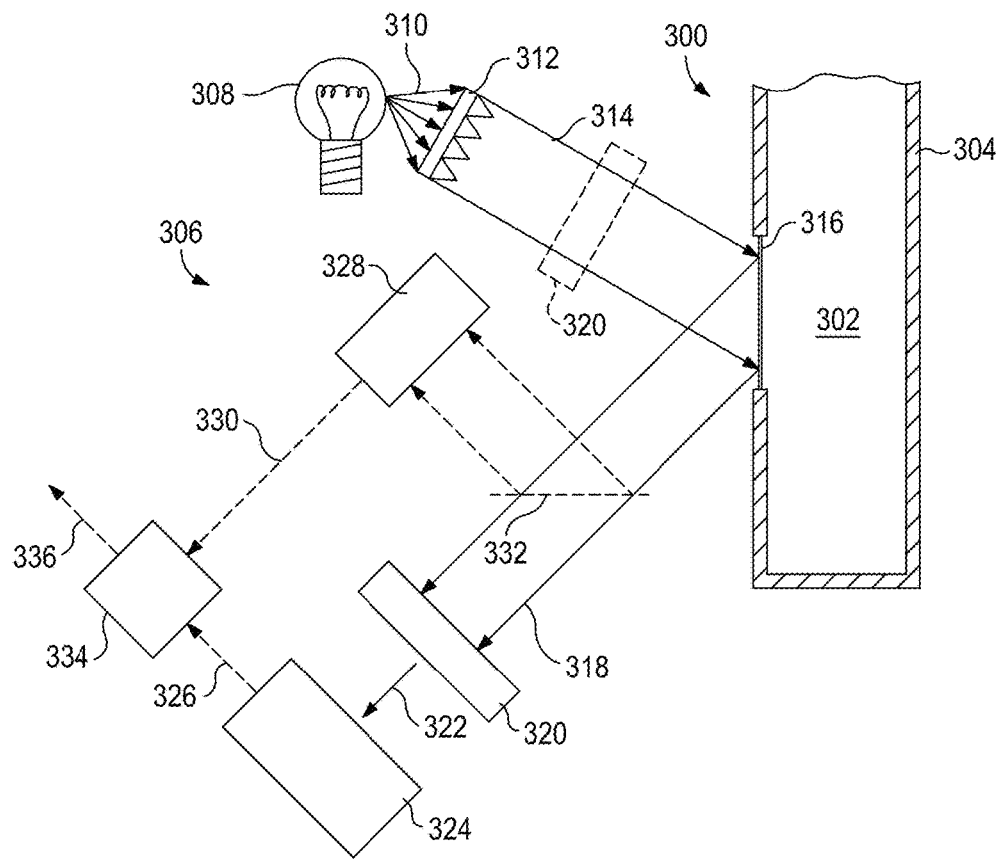
FIG. 3 illustrates an exemplary system for monitoring a cement additive present in a container, according to one or more embodiments.

Referring now to FIG. 3, illustrated is an exemplary system 300 for monitoring a cement additive 302, according to one or more embodiments. In the illustrated embodiment, the cement additive 302 may be contained within an exemplary container 304. In at least one embodiment, the container 304 may be a mixer and the cement additive 302 present therein may be actively mixing while measurements are being taken. In at least one embodiment, the container 304 may be a cup or the like of a mobile device. As will be appreciated, however, in other embodiments the container 304 may be any other type of container, as generally described or otherwise defined herein. For example, the container 304 may be a storage vessel or silo.

The system 300 may include at least one optical computing device 306, which may be similar in some respects to the optical computing device 200 of FIG. 2, and therefore may be best understood with reference thereto. While not shown, the device 306 may be housed within a casing or housing configured to substantially protect the internal components of the device 306 from damage or contamination from the external environment. The housing may operate to mechanically couple the device 306 to the container 304 with, for example, mechanical fasteners, brazing or welding techniques, adhesives, magnets, combinations thereof or the like.

As described in greater detail below, the optical computing device 306 may be useful in determining a particular characteristic of the cement additive 302 within the container 304, such as determining a concentration or absence/presence of an analyte present within the cement additive 302.

Knowing at least some of the characteristics of the cement additive 302 may aid in formulating a cement slurry with the desired setting characteristics. In turn, the cementing operation that utilizes the cement slurry may be more effective as premature setting or delayed setting may be mitigated. Further, the resultant set cement may be of higher quality because contaminants that affect set cement properties may be accounted for and counteracted before the cement slurry is placed in the formation.

In some embodiments, the device 306 may include an electromagnetic radiation source 308 configured to emit or otherwise generate electromagnetic radiation 310. The electromagnetic radiation source 308 may be any device capable of emitting or generating electromagnetic radiation, as defined herein. For example, the electromagnetic radiation source 308 may be a light bulb, a light emitting device (LED), a laser, a blackbody, a photonic crystal, an X-Ray source, combinations thereof, or the like. In some embodiments, a lens 312 may be configured to collect or otherwise receive the electromagnetic radiation 310 and direct a beam 314 of electromagnetic radiation 310 toward the cement additive 302. The lens 312 may be any type of optical device configured to transmit or otherwise convey the electromagnetic radiation 310 as desired. For example, the lens 312 may be a normal lens, a Fresnel lens, a diffractive optical element, a holographic graphical element, a mirror (e.g., a focusing mirror), a type of collimator, or any other electromagnetic radiation transmitting device known to those skilled in art. In other embodiments, the lens 312 may be omitted from the device 306 and the electromagnetic radiation 310 may instead be conveyed toward the cement additive 302 directly from the electromagnetic radiation source 308.

In one or more embodiments, the device 306 may also include a sampling window 316 arranged adjacent to or otherwise in contact with the cement additive 302 for detection purposes. The sampling window 316 may be made from a variety of transparent, rigid or semi-rigid materials that are configured to allow transmission of the electromagnetic radiation 310 therethrough. For example, the sampling window 316 may be made of, but is not limited to, glasses, plastics, semi-conductors, crystalline materials, polycrystalline materials, hot or cold-pressed powders, combinations thereof, or the like.

After passing through the sampling window 316, the electromagnetic radiation 310 impinges upon and optically interacts with the cement additive 302, including any analytes present within the cement additive 302. As a result, optically interacted radiation 318 is generated by and reflected from the cement additive 302. Those skilled in the art, however, will readily recognize that alternative variations of the device 306 may allow the optically interacted radiation 318 to be generated by being transmitted, scattered, diffracted, absorbed, emitted, or re-radiated by and/or from the cement additive 302, or one or more analytes present within the cement additive 302, without departing from the scope of the disclosure.

The optically interacted radiation 318 generated by the interaction with the cement additive 302 may be directed to or otherwise received by an ICE 320 arranged within the device 306. The ICE 320 may be a spectral component substantially similar to the ICE 100 described above with reference to FIG. 1. Accordingly, in operation the ICE 320 may be configured to receive the optically interacted radiation 318 and produce modified electromagnetic radiation 322 corresponding to a particular characteristic of interest of the cement additive 302. In particular, the modified electromagnetic radiation 322 is electromagnetic radiation that has optically interacted with the ICE 320, whereby an approximate mimicking of the regression vector corresponding to the characteristic of interest is obtained. In some embodiments, the characteristic of interest corresponds to the cement additive 302. In other embodiments, the characteristic of interest corresponds to a particular analyte found in the cement additive 302.

It should be noted that, while FIG. 3 depicts the ICE 320 as receiving optically interacted radiation 318 from the cement additive 302, the ICE 320 may be arranged at any point along the optical train of the device 306, without departing from the scope of the disclosure. For example, in one or more embodiments, the ICE 320 (as shown in dashed) may be arranged within the optical train prior to the sampling window 316 and equally obtain substantially the same results. In other embodiments, the sampling window 316 may serve a dual purpose as both a transmission window and the ICE 320 (i.e., a spectral component). In yet other embodiments, the ICE 320 may generate the modified electromagnetic radiation 322 through reflection, instead of transmission therethrough.

Moreover, while only one ICE 320 is shown in the device 306, embodiments are contemplated herein which include the use of at least two ICE 320 components in the device 306 configured to cooperatively determine the characteristic of interest in the cement additive 302. For example, two or more ICE 320 may be arranged in series or parallel within the device 306 and configured to receive the optically interacted radiation 318 and thereby enhance sensitivities and detector limits of the device 306. In other embodiments, two or more ICE 320 may be arranged on a movable assembly, such as a rotating disc or an oscillating linear array, which moves such that the individual ICE 320 components are able to be exposed to or otherwise optically interact with electromagnetic radiation 310 for a distinct brief period of time. The two or more ICE 320 components in any of these embodiments may be configured to be either associated or disassociated with the characteristic of interest in the cement additive 302. In other embodiments, the two or more ICE 320 components may be configured to be positively or negatively correlated with the characteristic of interest.

In some embodiments, it may be desirable to monitor more than one characteristic of interest at a time using the device 306. In such embodiments, various configurations for multiple ICE 320 components can be used, where each ICE 320 component is configured to detect a particular and/or distinct characteristic of interest corresponding, for example, to the cement additive 302 or an analyte in the cement additive 302. In some embodiments, the characteristic of interest can be analyzed sequentially using multiple ICE 320 components that are provided a single beam of optically interacted radiation 318 being reflected from or transmitted through the cement additive 302. In some embodiments, as briefly mentioned above, multiple ICE 320 components can be arranged on a rotating disc, where the individual ICE 320 components are only exposed to the beam of optically interacted radiation 318 for a short time. Advantages of this approach can include the ability to analyze multiple characteristics of interest within the cement additive 302 using a single device 306 and the opportunity to assay additional characteristics simply by adding additional ICE 320 components to the rotating disc corresponding to those additional characteristics.

In other embodiments, multiple devices 306 can be placed at a single location along the container 304, where each device 306 contains a unique ICE 320 that is configured to detect a particular characteristic of interest. In such embodiments, a beam splitter can divert a portion of the optically interacted radiation 318 being reflected by, emitted from, or transmitted through the cement additive 302 and into each device 306. Each device 306, in turn, can be coupled to a corresponding detector (e.g., detector 320) or detector array that is configured to detect and analyze an output of electromagnetic radiation from the respective optical computing device. Parallel configurations of optical computing devices can be particularly beneficial for applications that require low power inputs and/or no moving parts.

Those skilled in the art will appreciate that any of the foregoing configurations can further be used in combination with a series configuration in any of the present embodiments. For example, two devices 306 may be arranged in series, such as being located on or within a movable housing configured to perform an analysis at a single location in the container 304. Likewise, multiple detection stations, each containing devices 306 in parallel, can be placed in series for performing a similar analysis.

The modified electromagnetic radiation 322 generated by the ICE 320 may subsequently be conveyed to a detector 324 for quantification of the signal. The detector 324 may be any device capable of detecting electromagnetic radiation, and may be generally characterized as an optical transducer. In some embodiments, the detector 324 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 324 may be configured to produce an output signal 326 in real-time or near real-time in the form of a voltage (or current) that corresponds to the particular characteristic of interest in the cement additive 302. The voltage returned by the detector 324 is essentially the dot product of the optical interaction of the optically interacted radiation 318 with the respective ICE 320 as a function of the concentration of the characteristic of interest. As such, the output signal 326 produced by the detector 324 and the concentration of the characteristic of interest may be related, for example, directly proportional. In other embodiments, however, the relationship may correspond to a polynomial function, an exponential function, a logarithmic function, and/or a combination thereof.

In some embodiments, the device 306 may include a second detector 328, which may be similar to the first detector 324 in that it may be any device capable of detecting electromagnetic radiation. Similar to the second detector 216 of FIG. 2, the second detector 328 of FIG. 3 may be used to detect radiating deviations stemming from the electromagnetic radiation source 308. Undesirable radiating deviations can occur in the intensity of the electromagnetic radiation 310 due to a wide variety of reasons and potentially causing various negative effects on the output of the device 306. These negative effects can be particularly detrimental for measurements taken over a period of time. In some embodiments, radiating deviations can occur as a result of a build-up of film or material on the sampling window 316 which has the effect of reducing the amount and quality of light ultimately reaching the first detector 324. Without proper compensation, such radiating deviations could result in false readings and the output signal 326 would no longer be primarily or accurately related to the characteristic of interest.

To compensate for these types of undesirable effects, the second detector 328 may be configured to generate a compensating signal 330 generally indicative of the radiating deviations of the electromagnetic radiation source 308, and thereby normalize the output signal 326 generated by the first detector 324. As illustrated, the second detector 328 may be configured to receive a portion of the optically interacted radiation 318 via a beam splitter 332 in order to detect the radiating deviations. In other embodiments, however, the second detector 328 may be arranged to receive electromagnetic radiation from any portion of the optical train in the device 306 in order to detect the radiating deviations, without departing from the scope of the disclosure.

In some applications, the output signal 326 and the compensating signal 330 may be conveyed to or otherwise received by a signal processor 334 communicably coupled to both the detectors 324,328. The signal processor 334 may be a computer including a non-transitory machine-readable medium, and may be configured to computationally combine the compensating signal 330 with the output signal 326 in order to normalize the output signal 326 in view of any radiating deviations detected by the second detector 328. In some embodiments, computationally combining the output and compensating signals 326,330 may entail computing a ratio of the two signals 326,330. For example, the concentration or magnitude of each characteristic of interest determined using the optical computing device 306 can be fed into an algorithm run by the signal processor 334. The algorithm may be configured to make predictions on how the cement additive 302 or analytes therein will behave in a cement slurry or affect the properties of a resultant set cement.

In real-time or near real-time, the signal processor 334 may be configured to provide a resulting output signal 336 corresponding to the characteristic of interest. In some embodiments, as briefly discussed above, the resulting output signal 336 may be readable by an operator who can consider the results and make proper adjustments to the cement slurry formulation, if needed, based upon the magnitude of the measured characteristic of interest. In some embodiments, the resulting output signal 336 may be conveyed, either wired or wirelessly, to the user for consideration.

Systems similar to that illustrated in FIG. 3 may be useful in analyzing cement additives 302. For example, a system may include a probe that can be inserted into a cement additive 302 for analysis of a characteristic thereof. As such, the cement additive 302 may be contained within a container not having a device 306 connected thereto (e.g., a bag of cement additive 302 as shipped from a distributor). Further, the cement additive 302 may not be contained within a container, but rather may be a pile or mound of cement additive 302.

Figure 4:
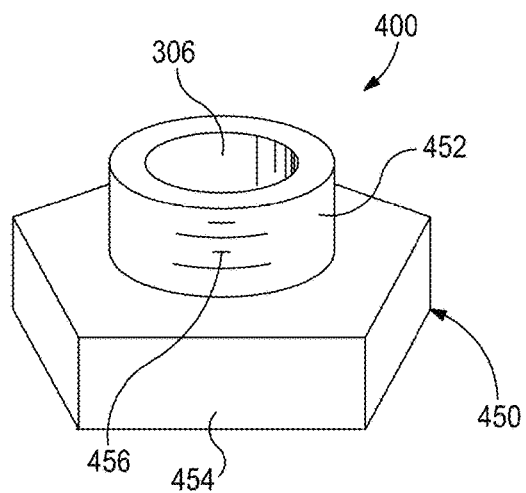
FIG. 4 illustrates an exemplary housing that may be used to house an optical computing device, according to one or more embodiments.

Referring now to FIG. 4, with continued reference to FIG. 3, illustrated is an exemplary housing 400 that may be used to house an optical computing device, according to one or more embodiments. In some embodiments, the housing 400 may be mechanically coupled to the container 304 using, for example, mechanical fasteners, brazing or welding techniques, adhesives, magnets, combinations thereof or the like. The housing 400 may be configured to substantially protect the internal components of the respective device 306 from damage or contamination from the external environment. Those skilled in the art, however, will readily recognize that several alternative designs and configurations of housings used to house the optical computing devices are suitable for the presently disclosed systems and methods. Indeed, the housing embodiments described and disclosed herein are by way of example only, and should not be considered limiting to the exemplary systems and methods disclosed herein.

As illustrated, the housing 400 may be in the general form of a bolt 450 which encloses the various components of an optical computing device, such as the device 306 of FIG. 3. In one embodiment, the components of the device 306 housed within the housing 400 may be generally housed within a stem 452 of the bolt 450, and the bolt 450 may have a hex head 454 for manual manipulation of the housing 400 using, for example, a wrench or other suitable torque-generating hand tool.

In at least one embodiment, the housing 400 defines external threads 456 that are threadable with corresponding mating pipe threads provided in, for example, an opening defined in the container 304 (FIG. 3) that is configured to receive the housing 400. The threads 456 may be sealed to the mating pipe threads with a thread sealant. The sampling window 316 is configured to be in optical communication with the cement additive 302 (FIG. 3) and allows optical interaction between the cement additive 302 and the other internal components of the internally-housed device 306.

Referring again to FIG. 3, those skilled in the art will readily recognize that, in one or more embodiments, electromagnetic radiation may be derived from the cement additive 302 itself, and otherwise derived independent of the electromagnetic radiation source 308. For example, various substances naturally radiate electromagnetic radiation that is able to optically interact with the ICE 320. In some embodiments, for example, the cement additive 302 or the substance within the cement additive 302 may be a blackbody radiating substance configured to radiate heat that may optically interact with the ICE 320. In other embodiments, the cement additive 302 or an analyte within the cement additive 302 may be radioactive or chemo-luminescent and, therefore, radiate electromagnetic radiation that is able to optically interact with the ICE 320. In yet other embodiments, the electromagnetic radiation may be induced from the cement additive 302 or the substance within the cement additive 302 by being acted upon mechanically, magnetically, electrically, combinations thereof, or the like. For instance, in at least one embodiment, a voltage may be placed across the cement additive 302 or the substance within the cement additive 302 in order to induce the electromagnetic radiation. As a result, embodiments are contemplated herein where the electromagnetic radiation source 308 is omitted from the particular optical computing device.

The foregoing systems and variations thereof may be suitable for methods that involve analyzing cement additives (e.g., measuring at least one characteristic of interest of at least one cement additive), which may be used in developing a cement slurry formulation.

In some instances, the amount of a cement additive in a cement slurry formulation may be based on the analysis of the cement additive. For example, the concentration of the active component(s) in the cement additive may be analyzed, where the amount of the cement additive in the cement slurry formulation is based on the concentration of the active components(s). In another example where the cement slurry additive includes two or more active components, the relative concentrations of at least some of the two or more active components may be analyzed, where the amount of the cement additive in the cement slurry formulation is based on the relative concentrations analyzed. In yet another example where the cement additive is in the form of a liquid concentrate with an active component(s) dispersed in a fluid, the concentration, the active component in the fluid may be analyzed and used in determining an amount of the cement additive to include in the cement slurry formulation. In other examples, the concentration of a degradation product of the cement additive or a contaminant in the cement additives may be analyzed, where the amount of the cement additive in the cement slurry formulations is based on that analysis.

In some instances, the amount of a second cement additive in a cement slurry formulation may be based on the analysis of a first cement additive. For example, the concentration of the active component(s) in the first cement additive, a degradation product of the first cement additive, a contaminant in the first cement additives, or a combination thereof may be analyzed, where the amount of the second cement additive in the cement slurry formulation is based on the analysis of the first cement additive.

In some instances, a combination of the foregoing examples may be performed. Accordingly, two or more ICE may be used in analyzing the cement additive.

Specific examples of analyses may include the following. Where the cement additive is a water source used to produce the cement slurry, the magnesium salt concentration, the total salt concentration, the pH, or a combination thereof may be analyzed. Then, another water source may be included in the cement slurry formulation to decrease the magnesium salt concentration, the total salt concentration, or both. To adjust the pH, an acid or a base may be used in the cement slurry formulation. Additionally or alternatively, cement slurry formulation adjustments may be made relative to the amount of other cement additives that are pH sensitive. For example, an acidic fluid may consume a portion of the lime in a cement slurry, thereby retarding the set time. Accordingly, the cement slurry formulation may be adjusted to include more lime, include a set accelerator, or both.

In another example, the characteristic of interest in the cement additive may be clay concentration. Generally, clay behaves similar to that of a gelling agent. Therefore, the concentration of the gelling agent in the cement slurry formulation may be adjusted based on the concentration of clay in one or more cement additives.

In yet another example, the characteristic of interest in the cement additive may be the concentration of organic matter (e.g., humic acid, lignins, hydroxycarboxylic acids, cellulose, saccharides, carbohydrates such as pentoses, hexoses and aldonic acids). Generally, organic matter retards cement set time, so a set accelerator may be used to counteract the presence of organic matter in cement additives.

In another example, salt can retard or accelerate set time of the cement slurry depending on concentration. Generally, below about 8% salt, cement slurry set time may be accelerated, and above about 8% salt cement slurry set time may be retarded. Accordingly, measurement of the salt concentration in one or more cement additives, especially the water, may be used to estimate the salt concentration in the cement slurry formulation. Then, the cement slurry formulation may be adjusted accordingly, for example, by adjusting the concentration of a set accelerator or a set retarder, by adding salt, or by removing salt by using a different cement additive with less salt.

After a cement slurry formulation has been developed or determined, a cement slurry may be prepared based on the cement slurry formulation. The cement slurry may then be implemented (e.g., introduced into a wellbore penetrating a subterranean formation for a primary cementing operation, a secondary cementing operation, or a remedial cementing operation).

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM, and flash EPROM.

Embodiments disclosed herein include Embodiment A, Embodiment B, and Embodiment C.

Embodiment A

A method that includes optically interacting a cement additive with an ICE configured to detect a characteristic of the cement additive; generating an output signal corresponding to the characteristic of the cement additive detected by the ICE; receiving and processing the output signal with a signal processor to yield a value for the characteristic of the cement additive; and determining an amount of the cement additive for use in producing a cement slurry based on the value of the characteristic of the cement additive.

Embodiment A may have one or more of the following additional elements in any combination: Element A1: wherein the characteristic of interest is a concentration of an active component of the cement additive; Element A2: wherein the characteristic of interest is a concentration of a degradation product of the cement additive; Element A3: wherein the characteristic of interest is a concentration of a contaminant of the cement additive; Element A4: wherein the cement additive is in the form of a liquid concentrate with an active component of the cement additive dispersed in a fluid and the characteristic of interest is a concentration of the active component in the fluid; Element A5: wherein the cement additive includes two or more active components, and wherein the characteristic of interest is a relative concentration of the two or more active components in the cement additive; Element A6: wherein the characteristic of the cement additive is a first characteristic of the cement additive, the method further comprising: optically interacting the cement additive with a second ICE configured to detect a second characteristic of the cement additive that is different than the first characteristic of the cement additive; generating a second output signal corresponding to the second characteristic of the cement additive detected by the second ICE; and receiving and processing the second output signal with the signal processor to yield a value for the second characteristic of the cement additive, wherein determining the amount of the cement additive for use in producing the cement slurry is based on the values for the first and second characteristics of the cement additive; Element A7: Element A6 wherein the cement additive is produced water, seawater, or saltwater, wherein the first characteristic is magnesium salt concentration and the second characteristic is pH; Element A8: Element A6 wherein the cement additive is produced water, seawater, or saltwater, wherein the first characteristic is magnesium salt concentration and the second characteristic is total salt concentration; Element A9: wherein optically interacting the cement additive with the ICE is performed at a well site; and Element A10: the method further including preparing the cement slurry; and introducing the cement slurry into a wellbore penetrating a subterranean formation.

By way of non-limiting example, exemplary combinations applicable to Embodiment A include: Element A6 in combination with two of Elements A1-A5 where more than two ICE may be utilized as needed to detect characteristics of interest; Element A9 in combination with at least one of Elements A1-A8; and Element A10 in combination with at least one of Elements A1-A9.

Embodiment B

A method that includes optically interacting a first cement additive with an ICE configured to detect a characteristic of the first cement additive; generating an output signal corresponding to the characteristic of the first cement additive detected by the ICE; receiving and processing the output signal with a signal processor to yield a value for the characteristic of the first cement additive; and determining a concentration of a second cement additive for use in producing a cement slurry based on the value of the characteristic of the first cement additive.

Embodiment B may have one or more of the following additional elements in any combination: Element B1: wherein the characteristic of interest is magnesium salt concentration, wherein the first cement additive is produced water, seawater, or saltwater, and wherein the second cement additive is another water source; Element B2: wherein the characteristic of interest is clay concentration and the second cement additive is a gelling agent; Element B3: wherein the characteristic of interest is organic matter and the second cement additive is a set accelerator; Element B4: wherein the first cement additive is water and the characteristic of interest is salt concentration, and wherein the method further includes calculating an estimated salt concentration in the cement slurry based at least in part on the salt concentration in the water; Element B5: Element B4 wherein the estimated salt concentration in the cement slurry is greater than 8% and the second cement additive is a set accelerator; Element B6: Element B4 wherein the estimated salt concentration in the cement slurry is less than 8% and the second cement additive is a set retarder; Element B7: wherein optically interacting the cement additive with the ICE is performed at a well site; and Element B8: the method further including preparing the cement slurry; and introducing the cement slurry into a wellbore penetrating a subterranean formation.

By way of non-limiting example, exemplary combinations applicable to Embodiment B include: at least two of Elements B1-B4 in combination where two or more ICE may be utilized as needed to detect characteristics of interest and optionally in combination with one of Elements B5 or B6; at least one of Elements B7-B8 in combination with the foregoing; and at least one of Elements B7-B8 in combination with one of Elements B1-B6.

Embodiment C

A method that includes at a well site optically interacting a cement additive with at least one integrated computational element ("ICE") configured to detect a characteristic of the cement additive, wherein the characteristic of interest is selected from the group consisting of: a concentration of an active component of the cement additive, a concentration of a degradation product of the cement additive, a concentration of a contaminant of the cement additive, and a relative concentration of a first active component of the cement additive to a second active component of the cement additive; generating an output signal corresponding to the characteristic of the cement additive detected by the at least one ICE; receiving and processing the output signal with a signal processor to yield a value for the characteristic of the cement additive; determining an amount of the cement additive for use in producing a cement slurry based on the value of the characteristic of the cement additive; preparing the cement slurry; and introducing the cement slurry into a wellbore penetrating a subterranean formation.

Therefore, the exemplary embodiments described herein are well adapted to attain the ends and advantages mentioned as well as those that are inherent therein. The particular embodiments disclosed above are illustrative only, as the exemplary embodiments described herein may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The invention claimed is:

1. A method comprising:
    optically interacting a cement additive with a first integrated computational element ("ICE") configured to detect a first characteristic of the cement additive, wherein the cement additive includes two or more active components, and wherein the first characteristic is a relative concentration of the two or more active components in the cement additive;
    generating an output signal corresponding to the first characteristic of the cement additive detected by the first ICE;
    receiving and processing the output signal with a signal processor to yield a value for the first characteristic of the cement additive; and
    determining an amount of the cement additive for use in producing a cement slurry based, at least in part, on the value of the first characteristic of the cement additive.

2. The method of claim 1, wherein the first ICE or a second ICE is configured to detect a second characteristic which is a concentration of a degradation product of the cement additive.

3. The method of claim 1, wherein the first ICE or a second ICE is configured to detect a second characteristic which is a concentration of a contaminant of the cement additive.

4. The method of claim 1, wherein the cement additive is a liquid concentrate with an active component of the cement additive dispersed in a fluid, wherein the first ICE or a second ICE is configured to detect a second characteristic which is a concentration of the active component in the fluid.

5. The method of claim 1, wherein the first ICE is configured to detect a relative concentration of a first active component of the two or more active components in the cement additive and a second ICE is configured to detect a relative concentration of a second active component of the two or more active components in the cement additive.

6. The method of claim 1, wherein optically interacting the cement additive with the first ICE is performed at a well site.

7. The method of claim 1, further comprising:
    optically interacting the cement additive with a second ICE configured to detect a second characteristic of the cement additive that is different than the first characteristic of the cement additive;
    generating a second output signal corresponding to the second characteristic of the cement additive detected by the second ICE; and
    receiving and processing the second output signal with the signal processor to yield a value for the second characteristic of the cement additive, wherein determining the amount of the cement additive for use in producing the cement slurry is based on the values for the first and second characteristics of the cement additive.

8. The method of claim 7, wherein the cement additive is produced water, seawater, or saltwater, and wherein the first characteristic is magnesium salt concentration and the second characteristic is pH.

9. The method of claim 7, wherein the cement additive is produced water, seawater, or saltwater, and wherein the first characteristic is magnesium salt concentration and the second characteristic is total salt concentration.

10. The method of claim 1, further comprising:
    preparing the cement slurry; and
    introducing the cement slurry into a wellbore penetrating a subterranean formation.

11. A method comprising:
    optically interacting a first cement additive with a first integrated computational element ("ICE") configured to detect a first characteristic of the first cement additive, wherein the first characteristic is at least one of magnesium salt concentration, clay concentration, salt concentration, and organic matter;
    generating an output signal corresponding to the first characteristic of the first cement additive detected by the first ICE;
    receiving and processing the output signal with a signal processor to yield a value for the first characteristic of the first cement additive; and
    determining a concentration of a second cement additive for use in producing a cement slurry based on the value of the first characteristic of the first cement additive, wherein the second cement additive is at least one of water, a gelling agent, a set accelerator, and a set retarder.

12. The method of claim 11, wherein the first cement additive is produced water, seawater, or saltwater, wherein the second cement additive is another water source.

13. The method of claim 11, wherein the first cement additive is water and the method further comprises calculating an estimated salt concentration in the cement slurry based at least in part on the salt concentration in the water.

14. The method of claim 13, wherein the estimated salt concentration in the cement slurry is greater than 8% and the second cement additive is a set accelerator.

15. The method of claim 13, wherein the estimated salt concentration in the cement slurry is less than 8% and the second cement additive is a set retarder.

16. The method of claim 11, further comprising:
    preparing the cement slurry; and
    introducing the cement slurry into a wellbore penetrating a subterranean formation.

17. An apparatus comprising:
    a first integrated computational element configured to optically interact with a cement additive to detect a first characteristic of the cement additive, wherein the cement additive is a liquid concentrate with a first active component of the cement additive dispersed in a fluid, wherein the first characteristic is a concentration of the first active component in the fluid;
    a processor;
    a computer-readable medium with instructions executable by the processor to cause the apparatus to,
        receive and process an output signal corresponding to the first characteristic of the cement additive detected by the first integrated computational element to yield a value for the first characteristic of the cement additive; and determine an amount of the cement additive for use in producing a cement slurry based on the value of the first characteristic of the cement additive.

18. The apparatus of claim 17 further comprising a second integrated computational element configured to optically interact with the cement additive to detect a second characteristic of the cement additive.

19. The apparatus of claim 18, wherein the cement additive comprises a second active component, wherein the second characteristic is a concentration of the second active component.

* * * * *